United States Patent [19]

Sievertsson et al.

[11] 4,054,557
[45] Oct. 18, 1977

[54] GROWTH PROMOTING POLYPEPTIDES AND PREPARATION METHOD

[75] Inventors: Hans Uno Sievertsson, Sollentuna; Linda Fryklund, Kungsangen; Knut Öivind Uthne, Sodertalje, all of Sweden

[73] Assignee: AB Kabi, Stockholm, Sweden

[21] Appl. No.: 470,040

[22] Filed: May 15, 1974

[51] Int. Cl.$^2$ .............................................. C08H 1/00
[52] U.S. Cl. ............................ 260/112 R; 260/112 B
[58] Field of Search ........................ 260/112 B, 112 R

[56] References Cited

U.S. PATENT DOCUMENTS

| | | | |
|---|---|---|---|
| 3,128,228 | 4/1964 | Michl | 260/112 B X |
| 3,201,382 | 8/1965 | Bornstein | 260/112 |
| 3,503,950 | 3/1970 | Li | 260/112 |
| 3,842,061 | 10/1974 | Andersson et al. | 260/112 B |

OTHER PUBLICATIONS

J. Am. Chem. Soc., vol. 72, 1950, pp. 465–474, Cohn et al.
J. Am. Chem. Soc., vol. 71, 1949, pp. 541–550, Oncley et al.
J. Biol. Chem., vol. 233, 1958, pp. 637–642, Lieberman et al.
Nature, vol. 201, 1964, Tozer et al., pp. 375–378.
Chem. Abstracts, vol. 53, 1960, 15458g-h, Eagle.
Chem. Abstracts, vol. 64, 1966, 6938c-d, Michl.
Chem. Abstracts, vol. 67, 1967, 19178u, Healy et al.

*Primary Examiner*—Harold D. Anderson
*Assistant Examiner*—E. A. Nielsen
*Attorney, Agent, or Firm*—A. A. Orlinger

[57] ABSTRACT

The application discloses (A) a growth-promoting polypeptide having molecular weight from about 5,000 to about 7,000 chromatographic mobility under electrophoresis from about 0.25 to about 0.37 relative to lysine at pH 5 and from about 0.17 to about 0.43 relative to aspartic acid at pH 7.5, terminal amino acid at its amino end being asparagine or aspartic acid, and respective amounts of aspartic acid, threonine, serine, glutamic acid, proline, glycine, alanine, valine, leucine, tyrosine, phenylalanine, lysine, arginine, trypophan, and cysteine or carboxymethyl cysteine, and also a couple of instances also methionine, isoleucine and histidine; and (B) the derivation of the polypeptides from blood serum or plasma or a plasma fraction by combined steps of (a) homogenizing the starting material in water, (b) admixing a solution of hydrochloric acid in ethanol thereby splitting the polypeptide from its carrier proteins and precipitating them, (c) adjusting the pH to 8.4 to provide a precipitate, (d) separating it, (e) adjusting the pH of the liquid residue to 3, (f) admixing a water-insoluble strongly acidic cation exchange matrix of sulfopropyl-oxygen-linked-substituted dextran cross-linked with epichlorhydrin at pH 3, (g) separating the gel matrix from the liquid, (h) eluting the polypeptide-containing material from the matrix with (x) ammonium acetate at pH 10 or (y) 0.75M ammonium bicarbonate; and (i) precipitating the polypeptide by admixing acetone.

16 Claims, No Drawings

GROWTH PROMOTING POLYPEPTIDES AND PREPARATION METHOD

This invention is that of individual growth-promoting polypeptides, each of which has a molecular weight in the range of from about 5,000 to about 7,500, and chromatographic mobility under electrophoresis relative to lysine at pH 5 of from about 0.25 to about 0.37 and relative to aspartic acid at pH 7.5 of from about 0.17 to about 0.43, and the terminal amino acid at the amino end of which polypeptide is asparagine or aspartic acid. The molecular weights herein and in the appended claims are determined by gel filtration enhanced by using a marker (e.g. insulin) with a known molecular weight of an order suitable for use as a standard for comparison with the claimed polypeptide.

The polypeptides of the invention are called growth-promoting polypeptides because, for example, they show medical importance is treating abnormal (such as retarded) growth conditions in humans as well as in farm animals, and also increase cell growth in in vitro cell cultures. For convenience, these growth-promoting polypeptides are referred to briefly as GPpeptides or GPPs or singly as GPpeptide or GPP.

The invention includes also the method of deriving these individual polypeptides from blood plasma, plasma fractions containing them, such as the Cohn fraction IV and Cohn solution IV-6+7 which are described in Cohn et al., Journ.Amer.Chem. Soc., volume 72 (1950) pp. 465 etc., and blood serum. The serum and plasma (providing the applicable plasma fractions starting material), from which these growth-promoting polypeptides are derived, are obtained from human or other mammalian animal (for example, bovine such as cow, equine such as horse, or porcine such as hog) blood.

The GPpeptides of the invention, in addition to having applicability in treating abnormal growth conditions, are useful to stimulate sulfate group incorporation as into proteoglycans of chick cartilage. For example, doses as small as 10 to 20 nanograms (ng.) of the specific GPP per ml. readily stimulate sulfate uptake. Then also, as little as from about 100 to 800 ng. of the selected GPP per ml. of cell culture provoke enhanced growth of any of the animal tissue cells that are cultivated in vitro such as human adult glia-cells, embryonic meningocytes, lung fibroblasts, and embryonic rat cells.

The just above noted low effective doses show the GPpeptides of the invention to be very potent. They thus are markedly useful as stimulators in tissue cultivation by serving to enhance the yield and quality of medically important substances such as vaccines, interferons, and other. These GPpeptides also are biologically characterized by their effectiveness in stimulating (i) deoxyribonucleic acid (DNA) and ribonucleic acid (RNA) synthesis in (human or other animal origin) cell cultures and (II) thymidine, uridine, sulfate, and amino acid transport into DNA, RNA, and proteins of the cartilage.

The method of deriving these individual GPpeptides from the starting material mammalian blood serum or plasma or plasma fraction containing them involves dispersing the selected starting material in water and therein subjecting that material advantageously simultaneously to (i) a bond-splitting sufficient amount of a compatible acid, bond-linkage-splitting agent to split and disaggregate these GPpeptides from their aggregation with their carrier proteins, and (ii) a water miscible lower alkanol (such as 96 % ethanol) to precipitate the proteins and adjusting the pH of the disperson to enhance that, separating the precipitate from the thus alkaline ethanol solution, decanting the final supernatant, leaving the precipitate as discarded, and adjusting the supernatant to pH 3 (as by slowly admixing concentrated hydrochloric acid).

The thus acidified supernatant then is contacted with a cation - removing sufficient amount of a compatible cation exhanger resin such as (the later below more fully described) sulfopropyl-SEPHADEX-25 (equilibrated with 0.1-M NaCl at pH 3) for a sufficient time. The cation exchanger is separated from the acid aqueous vehicle (as by filtration, beneficially with compatible washing), and the adsorbed active material is removed from the exchanger as by desorption or elution with a polypeptide-eluting sufficient amount of a compatible alkaline, polypeptide-eluting agent solution.

Admixing a compatible water-soluble polypeptide-precipitant (e.g. acetone) at from about $-12°$ C. to about $-18°$ C., and optimally at about $-15°$ C., with this eluate solution yields a precipitate which when washed with the precipitant and separated from the solution is a first stage or low activity or potency grade of these GPpeptides.

Alternatively, the final supernatant described on page 2, line25, is precipitated with 4 volumes of acetone-water prechilled at $-16°$ C. The supernatant is decanted off and discarded and the precipitate is a first stage or low activity or potency grade of these GPpeptides.

This first stage precipitate then is extracted with a polypeptide-dissolving sufficient amount of a compatible, water-soluble polypeptide-extracting agent such as a water-soluble lower aliphatic acid as formic acid, followed by separating the insoluble residue, for example, by centrifugation (at between about 4,000 and 6,000 r.p.m. and optimally at 5,000 r.p.m.), and subjecting the resulting supernatant liquid to gel chromatography or gelfiltration, as through a column packed with a suitable water-insoluble finely divided chromatographic agent as (the further below more fully described) SEPHADEX G-75 or G-50 equilibrated, for example, with 1 % (volume by volume) aqueous formic acid.

As a third embodiment of the gel chromatography or gelfiltration of the supernatant from the foregoing formic acid extraction, the effluent from the gelfiltration with the SEPHADEX G-75 is subjected to further similar gelfiltration through a column packed with SEPHADEX G-50 (fine particles of diameter range from 20 to 80 microns). Each of these three separate gelfiltrations (through the SEPHADEX G-75, through the SEPHADEX G-50, and the effluent of the G-75 filtration further filtered on the fine particle SEPHADEX G-50) includes separately in each of them collecting serially effluent fractions of a particular volume, e.g. 1, 2.3, 4, 6 and so on even up to 25 to 30 ml. each, and bioassaying groups of pooled serial samples to ascertain in what part of the effluent the active GPpeptide material occurs. The bioassay conveniently is conducted according to the more appropriate methods referred to below. Thus, these separate gelfiltration embodiments provide from the supernatant from the formic acid extraction of the first stage precipitate a second stage or improved activity or potency grade of these active GPpeptides.

In the next (the third) stage of the process, each of the dried (e.g. under vacuum) pooled fractions of the improved activity or potency grade of these active GPpeptides of a separate one of the just earlier above-described three separate gelfiltration embodiments of the second stage of the process is dissolved in a separate batch of, for example, from 200 to 400 mg. in 2 ml. of 0.025 M N-ethyl morpholine acetate buffer (i.e. 0.025 M N-ethyl-morpholine admixed with 0.015M acetic acid) and applied to a zone electrophoresis column (2 cm. diameter by 100 cm. high) packed with medium flow zone electrophoresis grade cellulose powder (e.g. Munktell No. 410, product of Grycksbo Pappersbruk Aktiebolag, Grycksbo, Sweden), ethanolysed cotton linters extracted with water, pyridine and ethanol, (see J. Porath, Science Tools volume II, No. 2, August, 1964), and subjected to zone electrophoresis using 0.05 M N-ethyl morpholine acetate buffer (i.e. 0.05M N-ethyl morpholine admixed with 0.03M acetic acid) at pH 7.5 as the elution solvent.

In each of these separate alkaline condition zone electrophoresis operations serial fractions of, for example, 4 ml. each of the effluent are collected at a suitable flow rate such as 40 ml./hr. and groups of pooled serial fractions are bioassayed. This basic condition zone electrophoresis thus yields a third stage further improved activity grade of these active GPpeptides.

In a fourth stage of the process, pooled fractions of the further improved activity grade of these active GPpeptides are dissolved in separate batches, for example, of from 50 to 200 mg. of the dried (e.g. under vacuum) GPpeptides in 2 ml. of 0.025M pyridine acetate buffer (0.025M pyridine admixed with 0.025M acetic acid), and applied to an analytical column (1 cm. diameter by 100 ml. high) packed with zone electrophoresis grade cellulose powder (e.g. the same as above Munktell No. 410 cellulose powder and subjected to acid condition electrophoresis using 0.05M pyridine acetate buffer (0.05M pyridine admixed with 0.05M acetic acid) at pH 5 as the elution solvent.

In this acid condition zone electrophoresis serial fractions of, for example, 1 ml. are collected at a suitable flow such as 15 ml./hr. and groups of serial fractions are pooled and bioassayed. Thus, from the pooled group of fractions showing active material content this acid condition zone electrophoresis yields a high level activity or potency grade of these active GPpeptides.

In a further embodiment (conveniently referred to as the fifth stage) of the method, individual amounts such as from 3 to 25 mg. each of this (dried, e.g. under vacuum) high level activity grade of GPpeptides are dissolved separately in a suitable amount of dilute aqueous mineral acid, as in 1 ml. of 0.02N hydrochloric acid and subjected to gelfiltration through an analytical gelfiltration column using the same acid solution as solvent. Effective serial size samples are collected at a suitable effluent flow rate.

Thus, upon applying to that analytical gelfiltration column one pooled group of active fractions from the stage 4 effluent, one top level specific active GPpeptide is obtained in one pooled group of effluent active fractions in this fifth stage; subjecting to that acid gelfiltration a second pooled group of active fractions from the stage 4 effluent provides in a second group of pooled effluent active fractions of the fifth stage a second top level specific active GPpeptide; and in the same way a third pooled group of active fractions from the stage 4 effluent provides in a third group of pooled effluent active fractions from this acid gelfiltration a third top level activity specific GPpeptide.

The GPpeptides of the invention and the method of deriving them are illustrated by, but not restricted to, the following examples:

EXAMPLE 1

Derivation of Crude GPpeptides From Cohn Fraction IV 26 kg. of Cohn fraction IV (Cohn et al. above, p. 1 lines 15-16), containing 40 % solids, obtained from 1200 kg. of pooled human plasma were homogenized in 30 liters of distilled water at 4° C. for 15 to 20 hours. The resulting homogenate was subjected to bond-linkage-splitting by admixing a prechilled mixture of 2.23 liters of concentrated hydrochloric acid and 90 liters of ethanol while stirring for an hour at 0° C. The reaction mixture was adjusted to pH 8.4 by admixing the required amount of 4m sodium hydroxide, and then centrifuged.

a. The supernatant was decanted and adjusted to pH 3 by slowly admixing concentrated hydrochloric acid. The centrifuge precipitate was discarded. Into 100 liters of this supernatant (corresponding to 1200 liters of plasma used as starting material) there was admixed 1500 grams (dry basis) of the further below more fully described SP-SEPHADEX G-25 cation exchange resin equilibrated with 0.1M sodium chloride at pH 3, and the stirring was continued at 0° C. for 60 minutes. The mixture then was filtered through a Buchner funnel and the resin was washed with 20 liters of 0.1M sodium chloride at pH 3.

The crude GPpeptides-containing material adsorbed on the resin was removed from the resin by eluting the latter with 0.2M ammonium acetate adjusted to pH 10 by addition of 25 % ammonium hydroxide. Alternatively, the crude adsorbate also was removed from the resin by eluting it with 0.75M ammonium bicarbonate.

The first stage or low acitivity or potency grade of the GPpeptides was recovered from the eluate by admixing into it 4 volumes of acetone at −15° C. The thus precipitated GPpeptides material was filtered out, washed with cold acetone and dried under vacuum at room temperature. Its in vitro assay by the chick cartilage assay method showed its activity as 0.9 U/mg. of the product (dry weight). U is one unit and is equal to 1 ml. of a standard serum containing approximately 0.007 U/mg. dry weight.

b. Instead of the procedure marked a) above, the following step is also operable. After the centrifugation, the supernatant was precipitated with 4 volumes of a mixture of acetone-ethanol in a ratio of 5 to 3. The acetone-water mixture was prechilled to −16° C and the mixture was left at that temperature for 24 hours. Thereafter, the supernatant was discarded and the formed precipitate was collected representing an alternative first stage or low activity of potency grade of the GPpeptides.

This first stage or low activity grade of GPpeptides can be derived also (i) from Cohn fraction IV-6+7 by following the procedure as in Example 1, and (ii) from blood plasma or serum of the blood of a mammalian animal (p. 2 above, lines 11-15), for example, by treating the plasma or serum by an applicable procedure described in Cohn et al. (supra p. 1, lines 14-16) to obtain either of the Cohn fraction IV or fraction IV-6+7 and then continuing as in Example 1 above.

EXAMPLE 2

Refinement of Example 1 GPpeptides by Gelfiltration

Batches of the low activity GPpeptides product of Example 1 were extracted with 20% formic acid in the proportion of 200 ml. of this acid solution per 100 grams (dry weight) of the product of Example 1. The mixture then was centrifuged at 5,000 r.p.m. at ambient temperature and the supernatant was decanted, and the precipitate again was extracted with the same ratio of the 20 % formic acid solution. This second mixture was likewise centrifuged, and the pooled decanted supernatants (the precipitate having been discarded) were subjected to gelfiltration by ascending gel chromatography.

a. A column ( 10 cm. in diameter and 100 cm. high) was packed with medium size SEPHADEX G-75 pre-swollen by being wetted with 1 % (volume by volume) aqueous formic acid and also equilbrated with this same formic acid solution. The pooled supernatants, approximately 710 ml. (corresponding to 1050 liters of original plasma), were applied to the gelfiltration column at 3° C. at a flow rate of 4 ml. per square cm. per hour; the column previously having been calibrated with insulin (mol.wt. 5700). Results from the bioassays are given in Table 3.

b. Individual batches of about 500 mg. (dry weight) each of the GPpeptides-containing material (obtained from a number of runs of separate gelfiltrations as described in the just preceding paragraph) dissolved in 1 % formic acid separately respectively were applied on a column (2.5 cm. in diameter by 100 cm. high) packed with SEPHADEX G-50 (fine size) that previously had been preswelled with 1 % (vol./vol.) formic acid. Effluent fractions of 6 ml. each were collected at a flow rate of 25 ml. per hour and bioassayed. The active GPpeptides material was obtained between fractions 43 to 81. Results from the bioassays are given in Tables 1-3.

c. Alternatively, the pooled supernatants from the 20 % formic acid extraction and centrifugation were subjected to gelfiltration at 3° C. through a column (10 cm. in diameter by 100 cm. high) packed with medium size SEPHADEX G-50 (preswelled with 1 % formic acid, volume by volume, in distilled water).

The column previously was calibrated with insulin (as a marker) which was eluted between fractions 165 to 190. Fractions of effluent of 25 to 30 ml. were collected at a flow rate of 300 ml. per hour, and the respective fractions were pooled and bioassayed. The major peak showing GPpeptides activity was found in fractions 150 to 200. This gelfiltration thus provided a second stage or improved activity or potency grade of these active GPpeptides showing 91 U per mg. dry weight, as reported in Table 1.

EXAMPLE 3

Zone Electrophoresis of Example 2 GPpeptides At pH over 7

Separate batches of from 200 to 400 mg. (dry basis) each of the GPpeptides activity material obtained from each of the parts (a), (b) and (c) of Example 2 separately respectively were dissolved each alone in 2 ml. of 0.025M N-ethylmorpholine acetate buffer (p. 4, lines 5-6, above). Its resulting solution separately respectively was applied to a zone electrophoresis column (2 cm. in diameter by 100 cm.high) packed with medium fiber length Munktell No. 410 cellulose powder (p. 4, lines 6-8, above) and subjected to zone electrophoresis under 800 volts and 20 milliamperes, using 0.05M N-ethyl-morpholine buffer (p. 4, lines 11-13, above) at pH 7.5 as the elution solvent.

In each of these respectively separate alkaline condition zone electrophoresis runs serial fractions of 4 ml. each of the effluent were collected at a flow rate of 40 ml. per hour. Bioassays showed the GPpeptides activity material was collected between effluent fractions 45 to 55 and also fractions 57 to 66. This alkaline condition zone electrophoresis thus yields a third stage, further improved activity grade of the GPpeptides. Data from bioassays all given in Tables 1-3.

EXAMPLE 4

Zone Electrophoresis of Example 3 GPpeptides at pH Below 7

Separate pooled fractions in batches of from 50 to 200 mg. (dry basis) each of the GPpeptides active material from Example 3 separately respectively were dissolved each along in 2 ml. of 0.025M of pyridine acetate buffer (p. 4, lines 21-22, above). Its resulting solution separately respectively was applied to an analytical column (1 cm. in diameter by 100 cm. high) packed with the medium fiber length Munktell No. 410 cellulose powder and subjected to zone electrophoresis under 1000 volts and 10 milliamperes, using 0.05m pyridine acetate buffer (p. 4, lines 25-27, above) at pH 5 as the elution solvent.

In each of these respectively separate acid condition zone electrophoresis runs serial fractions of 1 ml. each of the effluent were collected at a flow rate of 15 ml. per hour. Bioassays showed that the GPpeptides active material was collected between fractions 15 to 18 and also fractions 23 to 40. This stage provides a high level activity grade of these active GPpeptides as shown in Tables 1 and 3.

EXAMPLE 5

Gelfiltration Refining of Example 4 GPPs Into Separate Ones

Separate batches of from 3 to 25 mg. (dry basis) each of the GPpeptides active material obtained in Example 4 were dissolved separately respectively in one ml. of 0.02M hydrochloric acid. Each such resulting solution separately respectively was applied on an analytical gelfiltration column (1.5 cm. in diameter by 88 cm. high) packed with fine SEPHADEX G-50 in 0.02N hydrochloric acid, and previously calibrated with insulin, and subjected to gelfiltration at room temperature. In calibrating the column with the insulin, the latter showed an elution maximum at its fraction 38. Fractions of 2.3 ml. of effluent each were collected at a flow rate 10 ml. per hour.

$GPP_1$:Thus, when the pooled effluent fractions 32-40 from Example 4 were subjected to this acid condition gelfiltration, the effluent fractions 35 to 40 (having a peak activity in fraction 37) provide one of the individual GPpeptides designated briefly as $GPP_1$. This specific polypeptide has a molecular weight of about 7,000, the terminal amino acid at its amino end is asparagine, and it is composed of the following combined amino acids, each in its respectively noted molar content per mol of this polypeptide: aspartic acid 4.1, threonine 4.3, serine 7.8, glutamic acid 5.1, proline 8.2, glycine 10.2, alanine 4.9, valine 4.0. methionine 0.3, isoleucine 1.3, leucine 2.1, tyrosine 0.6, phenylalanine 61, histidine 1.5, lysine 2.8, arginine 4.0, tryptophan 1.0, and carboxymethyl cysteine 1.0.

GPP₂: When the pooled effluent fractions 23 to 31 from the electrophoresis of Example 4 was subjected to this acid condition gelfiltration, the effluent fractions 35 to 40 (having a peak of activity in fraction 37) provide another individual GPpeptide designated GPP₂. The molecular weight of this one is about 7,000. The terminal amino acid at its amino end is asparagine, and it is composed of the following combined amino acids, each in its respectively noted molar content per mol of this polypeptide: aspartic acid 4.8, threonine 1.9, serine 3.5, glutamic acid 4.6, proline 7.3, glycine 7.1, alanine 7.0, valine 4.9, methionine 0.9, isoleucine 0.8, leucine 3.3, tyrosine 0.9, phenylalanine 2.2, histidine 3.8, lysine 2.5, arginine 4.6, tryptophan 1.0, and cysteine (determined as cysteic acid) 1.14.

GPP₃: Then when the pooled effluent fractions 15 to 18 from Example 4 were subjected to this acid condition gelfiltration, the effluent fractions 38 to 44 (having a peak of activity in fraction 41) provide GPP₃. This polypeptide has a molecular weight of about 5,000. The terminal amino acid at its amino end is aspartic acid, and it is composed of the following combined amino acids, each in its respectively noted molar content per mol of this polypeptide: aspartic acid 5.2, threonine 4.0, serine 3.1, glutamic acid 8.1, proline 0.8, glycine 2.1, alanine 1.1, valine 1.8, leucine 1.0, tryosine 2.9, phenylalanine 1.0, lysine 3.8, arginine 1.3, tryptophan 1.0, and carboxymethyl cysteine 8.0.

The relative mobility values of these three polypeptides were determined by electrophoresis at 400 volts and 200 milliamperes on medium flow Munktell electrophoresis paper 304 (product of the aforesaid Grycksbo Pappersbruk Aktiebolag, p. 4 lines 8–9 above). The mobility value of (i) GPP₁ relative to lysine at pH 5 was 0.29 and relative to aspartic acid at pH 7.5 was 0.17. (ii) GPP₂ relative to lysine at pH 5 was 0.37, and (iii) GPP₃ relative to aspartic acid at pH 5 was 0.25 and at pH 7.5 was 0.43. At each pH glycine was used as a marker and its mobility was determined as zero.

Each of the respectively separate end product GPpeptide species GPP₁, GPP₂ and GPP₃ of the three separate parts of Example 5 can be dried individually under vacuum at room temperature, just as was the end product GPpeptides of Example 1 (p. 6 lines 14 - 15 above) and also the individual end product GPpeptides of Examples 2 through 4 respectively (p. 3 line 30, p.5, lines 1–4, and page 4, lines 20–22 and p. 5, lines 3–5 above). Each of the different end product GPpeptides or GPP species of any of the examples or embraced by the invention also can be dried, for example, for storage by lyophilization (i.e. vacuum drying from the frozen state).

Then too, any of these GPpeptides or separate GPP species can be put up in pharmaceutical dosage forms as illustrated by, but not restrictd to, the following:

EXAMPLE 6

Buffered Solution of GPPs or a GPP in Ampuls:

a. In a sterile buffer solution containing 9 grams of sodium chloride and 25 ml. of 20 % albumin aqueous solution there is admixed 971 mg. of the GPpeptides of Example 3 and sufficient water added to make a total of a liter of final solution.

The GPpeptides-containing buffer solution is filtered through a bacteria tight MILLIPORE sintered glass filter after initially having prewashed it with 100 ml. of the buffer. The first 3 to 5 ml. of the filtered GPpeptide-containing buffer solution are discarded because of their lower concentration of active GPpeptides due to their dilution with buffer solution retained in the filter from this prewashing. The resulting filtered GPpeptide-containing filtered solution then was filled under sterile conditions into rubber-stoppered sterile ampuls to provide in each 100 ml. of GPpeptides-containing solution equivalent to 10,000 U per ampul or 100 U per ml. Thus, to administer from 10 to 30 units per dose requires canula-puncturing the sterilized rubber stopper to withdraw from the ampul 0.1 to 0.3 ml. per dose.

b. Admixing 374.5 mg of the 267 U/mg. GPpeptides of Example 4 into the buffer solution in part (a) of this example and sufficient water to make a total of a liter of final solution and filling it into ten of the same ampuls also provides in each of them 100 ml. of the GPpeptides solution containing 100 U per ml. Similarly withdrawing from such ampul from 0.1 to 0.3 ml. enables administering from 10 to 30 units respectively of that GPpeptides per dose.

The specific activity of the filtrate going into the ampuls can be determined by bioassay. The ampuls should be stored at $-20°$ C.

Corresponding injectable dosage forms of the GPpeptides of Example 2 and of any one of the three respectively separate polypeptide species of Example 5 can be prepared similarly and in any other desired strength (i.e. U per ml.) with the respective GPpeptides or polypeptide species and the foregoing buffer solution of this Example 6 or any equally compatible injectable buffer solution. Any of the GPpeptides or any individual polypeptide species also can be stored as a powder after drying it as by lyophilization.

Their effectiveness in growth promotion was shown, for example, after injection of growth promotion effective doses of the GPpeptide into 60 to 75 gram rats, following which an increase in tibial width was obtained. The tibia was prepared and measured according to Greenspan et al. in Endocrinology volume 45 (1949) page 455.

The SEPHADEX products used in the gelfiltration or gel chromatography steps of Examples 1, 2 and 5 are products of Pharmacia Fine Chemicals, of Uppsala, Sweden, and of Piscatawny, New Jersey, U.S.A. The SEPHADEX G-50 medium has a particle size range of from 50 to 150 microns, whereas the SEPHADEX g-50 fine differs in that its particle size ranges from 20 to 80 microns. The SEPHADEX G-75 particles range from 40 to 120 microns. The SP-SELPHADEX-25 is a strongly acidic cation exchange resin due to replacement of the hydrogen of the hydroxyl groups of the dextran molecule by the negatively charged sulfopropyl group ($-C_3H_6SO_3^{31}$).

Bioassay procedures.

The in vitro bioassay of GPP activity has been determined in cartilage as described by Hall (Acta Endocrinol volume 63 (1970) pp. 338 etc.). This method is based on the incorporation of labelled sulfate into proteoglycans of chick embryo cartilage. The bioassay data of GPP active material from different steps in the isolation procedure are summarized in Table 1.

GPP activity has been determined in cultures of human glia-like cells as described by Westermark et al. (Exp. Cell Res. volume 69 (1971) pp. 259 etc.). This method measures DNA synthesis using labelled thymidine. Stimulatory effects of a GPP preparation is in each test compared with that of different concentrations of calf serum. Examples of test data of different GPP preparations are summarized in Table 2.

Determination of GPP activity by the growth of human cells, cultivated at sub-optimal levels of calf serum in the growth medium.

Human cells are cultured in glass bottles with a culture surface of 45 cm² and a medium volume of 30 ml. The medium consists of a commercial available Eagle's MEM containing Earle's salt solution (Flow Laboratories). To the medium 100 IU/ml of benzylpenicillin, 100 γ/ml. of streptomycin, 2.25 mg/ml of N-tris(hydroxymethyl)methylglycine and 0.05 Methocel ® (methylcellulose product, Type MC), Dow Chemical Co., are added. Suitable concentrations of calf serum(CS) are added to this basal medium.

The culture flask is seeded with $0.8 - 1.0 \times 10^6$ cells that have been grown in the basal medium + 10 % CS. The cells are cultivated at 37° C in stoppered flasks for 4 to 5 days. Thereafter they are treated with 0.25 % trypsin, suspended in the basal medium and counted in a counting chamber.

Studies have been performed on human embryonic lung fibroblasts. In this type the basal medium + 1 % CS gives a reduction of growth of 60-70 % compared with optimal growth (basal medium + 10 % CS). Thus the cells are cultured in basal medium + 1 % CS with and without the GPP preparation. After 4 to 5 days the cells are trypsinized and the amount of cells per culture flask is determined. The GPP activity is given as per cent growth stimulation compared with the 1 % CS used as a control. Usually the obtained value is the mean value of two flasks. Data are summarized in Table 3.

Table 1.

In vitro assay of GPpeptides using the chick cartilage assay.

| Description | U/mg dry weight[a] |
|---|---|
| Example 1 | 0.9 |
| Example 2b | 26 |
| Example 2c | 91 |
| Example 3 | 103 |
| Example 4 | 267 – 417 |
| Example 5 | 720 – 930 |

[a]One unit = 1 ml. of a standard serum containing approximately 0.007 U/mg dry weight.

Table 2.

Test of GPpeptides in human glia-like cells.

| Description | Dosage GPP μg/ml | Stimulation in cpm a) | Stimulation in cpm of calf serum 0.25 % | 0.5 % | 1 % |
|---|---|---|---|---|---|
| Example 2 | 9.6 | 6091 6310 | 5424 6729 | | |
| Example 2b | 3.4 | 2289 2101 | | | 3825 4010 |
| Example 3 | 0.71 | 9815 11134 | | 10809 10278 | | a) The base uptake e.g. without the presence of GPP or calf serum varies between 600 - 1000 cpm.

Table 3.

CPpeptides of PPpeptides in human lung fibroblasts.

| GPP prep. | μg of GPP/ml. | Cells/flask × 10⁶ GPP + 1% CS | Cells/flask × 10⁶ 1% CS control | Growth stimulation of GPP per cent |
|---|---|---|---|---|
| Example 2a | 2.4 | 3.3 | 2.1 | 57 |
| Example 2b | 3.65 | 3.85 | 2.7 | 43 |
| Example 3 | 2.2 | 2.5 | 1.3 | 92 |
| Example 4 | 0.1 | 3.45 | 3.0 | 15 |

What is claimed is:

1. A growth-promoting polypeptide derivable from mammalian blood plasma by a procedure which includes subjecting the plasma material to an acid, bond-splitting agent; and having (i) molecular weight in the range of from about 5,000 to about 7,000 determined by gel filtration enhanced by using insulin as a standard for comparison, (ii) chromatographic mobility under electrophoresis relative to lysine at pH 5 of from about 0.25 to about 0.37 and relative to aspartic acid at pH 7.5 of from about 0.17 to about 0.43, and (iii) the terminal amino acid at its amino end is asparagine or aspartic acid, and also having the respective constitution provided by one of the following groups (a), (b), and (c) of combined amino acids, with each said acid being in its respectively noted molar content:

a. aspartic acid 4.1, threonine 4.3, serine 7.8, glutamic acid 5.1, proline 8.2, glycine 10.2, alanine 4.9, valine 4.0, methionine 0.3, isoleucine 1.3, leucine 2.1, tyrosine 0.6, phenylalanine 1.1, histidine 1.5, lysine 2.8, arginine 4.0, tryptophan 1.0, and carboxymethyl cysteine 1.0, per mol of said polypeptide;

b. aspartic acid 4.8, threonine 1.9, serine 3.5, glutamic acid 4.6, proline 7.3, glycine 7.1, alanine 7.0, valine 4.9, methionine 0.9, isoleucine 0.8, leucine 3.3, tyrosine 0.9, phenylalanine 2.2, histidine 3.8, lysine 2.5, arginine 4.6, tryptophan 1.0, and cysteine (determined as cysteic acid) 1.14, per mol of said polypeptide; and c. aspartic acid 5.2, threonine 4.0, serine 3.1, glutamic acid 8.1, proline 0.8, glycine 2.1, alanine 1.1, valine 1.8, leucine 1.0, tryosine 2.9, phenylalanine 1.0, lysine 3.8, arginine 1.3, tryptophan 1.0, and carboxymethyl cysteine 8.0, per mol of said polypeptide.

2. The growth-promoting polypeptide as claimed in claim 1, having (i) molecular weight of about 7,000, (ii) mobility under elctrophoresis relative to lysine at pH 5 of 0.29 and relative to aspartic acid at pH 7.5 of 0.17, (iii) asparagine as its said amino end terminal amino acid; and (iv) the composition provided by the following combined amino acids each in its respectively noted molar content: aspartic acid 4.1, threonine 4.3, serine 7.8, glutamic acid 5.1, proline 8.2, glycine 10.2, alanine 4.9, valine 4.0, methionine 0.3, isoleucine 1.3, leucine 2.1, tyrosine 0.6, phenylalanine 1.1, histidine 1.5, lysine 2.8, arginine 4.0, tryptophan 1.0, and carboxymethyl cysteine 1.0.

3. The growth-promoting polypeptide as claimed in claim 1 having (i) molecular weight of about 7,000, (ii) mobility under electrophoresis relative to lysine at 5 of 0.37, (ii) asparagine as its said amino end terminal amino acid; and (iv) the composition provided by the following combined amino acids each in its respectively noted molar content: aspartic acid 4.8, threonine 1.9, serine 3.5, glutamic acid 4.6, proline 7.3, glycine 7.1, alanine 7.0, valine 4.9, methionine 0.9, isoleucine 0.8, leucine 3.3, tyrosine 0.9, phenylalanine 2.2, histidine 3.8, lysine 2.5, arginine 4.6, tryptophan 1.0, and cysteine (determined as cysteic acid) 1.14, per mol of said polypeptide.

4. The growth-promoting polypeptide as claimed in claim 1, having (i) molecular weight of about 5,000, (ii) mobility under electrophoresis relative to aspartic acid at pH 5 of 0.25 and at pH 7.5 of 0.43, (iii) aspartic acid as its said amino end terminal amino acid; and (iv) the composition provided by the following combined amino acids each in its respectively noted molar content: aspartic acid 5.2, threonine 4.0, serine 3.1, glutamic acid 8.1, proline 0.8, glycine 2.1, alanine 1.1, valine 1.8, leucine 1.0, tryosine 2.9, phenylalanine 1.0, lysine 3.8, arginine 1.3, tryptophan 1.0, and carboxymethyl cysteine 8.0. per mol of said polypeptide.

5. In the method of deriving a growth-promoting polypeptide having molecular weight in the range of from about 5,000 to about 7,000, chromatographic mobility under electrophoresis relative to lysine at pH 5 of from about 0.25 to about 0.37 and relative to aspartic acid at pH 7.5 of from about 0.17 to about 0.43, and the terminal amino acid at its amino end being asparagine or aspartic acid, from mammalian blood serum or plasma or a plasma fraction from which said polypeptide can be derived, the combination of steps comprising (a) homogenizing the Cohn et al. plasma fraction IV or fraction IV-6+7 with sufficient water and for a time sufficient to homogenize said fraction, (b) subjecting the resulting homogenate with a sufficient polypeptide-to-protein-linkage -bond-splitting amount of a mixture of about 1 part of concentrated hydrochloric acid in about forty parts of about 96% ethanol at about 0° C for a time sufficient to split said polypeptide from its carrier proteins and to precipitate said proteins, (c) adjusting the pH of the reaction mixture to about 8.4 with the required amount of a compatible water-soluble alkali metal hydroxide, (d) separating the precipitate from the liquid vehicle, (e) adjusting the pH of said liquid vehicle to about 3 by cautiously admixing it with concentrated hydrochloric acid, (f) admixing the resulting acid liquid vehicle at about 0° C with a polypeptide-adsorbing sufficient amount of a finely divided, water-insoluble strongly acidic cation exchange gel matrix constituted of a three-dimensional network of sulfopropyl-oxygen-linked-substituted dextran chains cross-linked with epichlorhydrin equilibrated with sodium chloride at about pH 3, for a time sufficient to adsorb said polypeptide; (g) separating said water-soluble gel matrix with said adsorbed polypeptide from its surrounding liquid vehicle, (h) eluting the polypeptide containing material from said gel matrix with (x) about 0.2M ammonium acetate adjusted to pH 10 by addition of about 25% ammonium hydroxide, or (y) about 0.75M ammonium bicarbonate; and (i) precipitating the crude polypeptide from the resulting eluate by admixing the latter at about −15° C with about 4 times its volume of acetone.

6. The combination of steps as claimed in claim 5, wherein said crude polypeptide precipitate is separated from said alkaline acetone solution.

7. The combination of steps as claimed in claim 6, wherein said separated crude polypeptide precipitate is extracted with a growth promotion polypeptides extraction effective amount of an about 20% formic acid aqueous solution to extract the growth promotion polypeptides from said precipitate; the resulting extract of said polypeptides in said formic acid solution then is separated from the aqueous acetone-insoluble residue of said precipitate and subjected to gelfiltration at about 3° C through a gelfiltration column packed with a finely divided water-insoluble gel matrix constituted of a three-dimensional network of dextran chains cross-linked with epichlorhydrin.

8. The combination of steps as claimed in claim 7, wherein said finely divided gel matrix has a particle size of from about 50 to 150 microns and a water regain of 5±0.3 ml. of water per gm. of dry particles, and effluent fractions of 25 to 30 ml. each are collected at a flow rate of about 300 ml. per hour.

9. The combination of steps as claimed in claim 7, wherein said finely divided gel matrix has a particle size from about 40 to 120 and a water regain of from 7.5±0.5 ml. of water per gm. of dry particles; and said extract of said polypeptides is applied to said column at a flow rate of 4 ml. per sq. cm. per hour.

10. The combination of steps as claimed in claim 9, wherein the effluent from the gelfiltration therein is subjected to further gelfiltration through a column packed with a finely divided water-insoluble gel matrix constituted of a three-dimensional network of dextran chains cross-linked with epichlorhydrin and having a particle size of from about 20 to about 80 microns and a water regain of 5±0.3 ml. of water per gm. of dry particles; and effluent fractions of 6 ml. each are collected from said column at a flow rate of 25 ml. per hour.

11. The combination of steps as claimed in claim 8, wherein from about 200 to about 300 mg. of the solute of the pooled fractions 150 to 200 of claim 8 are dissolved in 2 ml. of 0.025M N-ethylmorpholine acetate buffer and subjected to column zone electrophoresis in a column packed with zone electrophoresis grade cellulose powder, under about 800 volts and about 20 milliamperes and using 0.05M N-ethylmorpholine acetate buffer at about pH 7.5 as the elution solvent.

12. The combination of steps as claimed in claim 11, wherein serial fractions of 4 ml. each of the effluent from said electrophoresis are collected at a flow rate of 40 ml. per hour.

13. The combination of steps as claimed in claim 12, wherein from about 50 to about 200 mg. of the solute of either of pooled effluent fractions 45 to 55 or 57 to 66 of claim 12 are dissolved in per 2 ml. of 0.025M of pyridine acetate buffer and subjected to column zone electrophoresis by being applied to an analytical column packed with medium fiber length zone electrophoresis grade of cellulose powder, under about 1000 volts at about 10 milliamperes and using 0.05M pyridine acetate buffer at pH 5 as the elution solvent.

14. The combination of steps as claimed in claim 13, wherein serial fractions of 1 ml. each of column effluent are collected at a flow rate of 15 ml. per hour.

15. The combination of steps as claimed in claim 14, wherein from about 3 to about 25 mg. of the solute of either of the pooled fractions 15 to 18 or the pooled fractions 23 to 40 of claim 14 are dissolved in per one ml. of 0.02M hydrochloric acid and applied to an analytical gelfiltration column packed with the finely divided gel matrix constituted of a threedimensional network of dextran chains cross-linked with epichlorhydrin, in 0.02N hydrochloric acid, and subjected to gelfiltration at ambient temperature; and serial fractions of about 2.3 ml. are collected at a flow rate of 10 ml. per hour; and (i) effluent fractions 35 to 40 of said gelfiltration of the pooled effluent fractions 32 to 40 of claim 14 are pooled as one final product, and (ii) effluent fractions 35 to 40 of said gelfiltration of the pooled effluent fractions 23 to 31 of claim 14 are pooled as a second final product, and (iii) effluent fractions 38 to 44 of said gelfiltration of the pooled effluent fractions 15 to 18 of claim 14 are pooled as a third final product.

16. The combination of steps as claimed in claim 10, wherein from 200 to about 300 mg. of the solute of the pooled fractions 43 to 81 of claim 10 are dissolved in 2 ml. of 0.025M N-ethylmorpholine acetate buffer and subjected to column zone electrophoresis in a column packed with zone electrophoresis grade cellulose powder, under about 800 volts and about 20 milliamperes and using 0.05M N-ethylmorpholine acetate buffer at about pH 7.5 as the elution solvent.

* * * * *